(12) United States Patent
Klett et al.

(10) Patent No.: US 12,414,735 B2
(45) Date of Patent: Sep. 16, 2025

(54) METHOD FOR DETECTING EPILEPTIC AND PSYCHOGENIC SEIZURES

(71) Applicant: LIFE SCIENCE INKUBATOR BETRIEBS GMBH & CO. KG, Bonn (DE)

(72) Inventors: Kevin Klett, Metzingen (DE); Florian Lutz, Stuttgart (DE); Julian Hofmeister, Tübingen (DE)

(73) Assignee: Life Science Inkubator Betriebs GmbH & Co. KG, Bonn (DE)

( * ) Notice: Subject to any disclaimer, the term of this patent is extended or adjusted under 35 U.S.C. 154(b) by 0 days.

(21) Appl. No.: 17/622,418

(22) PCT Filed: Aug. 28, 2020

(86) PCT No.: PCT/EP2020/074128
§ 371 (c)(1),
(2) Date: Dec. 23, 2021

(87) PCT Pub. No.: WO2021/038074
PCT Pub. Date: Mar. 4, 2021

(65) Prior Publication Data
US 2022/0354416 A1 Nov. 10, 2022

(30) Foreign Application Priority Data
Aug. 28, 2019 (EP) .................... 19194188

(51) Int. Cl.
*A61B 5/352* (2021.01)
*A61B 5/00* (2006.01)
*A61B 5/024* (2006.01)

(52) U.S. Cl.
CPC ........ *A61B 5/4094* (2013.01); *A61B 5/02405* (2013.01); *A61B 5/352* (2021.01)

(58) Field of Classification Search
None
See application file for complete search history.

(56) References Cited

U.S. PATENT DOCUMENTS

2007/0260147 A1* 11/2007 Giftakis ............... A61N 1/3962
600/483
2012/0046558 A1* 2/2012 Virag .................... A61B 5/352
600/300

OTHER PUBLICATIONS

Jonatas Pavei et al., "Early Seizure Detection Based on Cardiac Autonomic Regulation Dynamics", Frontiers in Physiology, Oct. 5, 2017, vol. 8, Article 765, pp. 1-12 (12 pages total).
(Continued)

*Primary Examiner* — Ankit D Tejani
(74) *Attorney, Agent, or Firm* — Sughrue Mion, PLLC (57) ABSTRACT

The invention relates to a method for detecting epileptic or psychogenic seizures, comprising the steps of:
a. recording a large number of temporally sequential parameter values for a parameter type, wherein a parameter value is determined on the basis of a series of temporally sequential RR intervals, the series of temporally sequential parameter values preferably differing in that the series that served as the basis for determining the following parameter value includes, in place of the oldest RR interval of the series that served as the basis for determining the preceding parameter value (preceding series), the RR interval temporally subsequent to the most recent RR interval of the preceding series,
b. comparing the time course of the parameter values with the time course of parameter values for the same parameter type that had been determined according to method step a, and the determination thereof is based on RR intervals that indicate a seizure (parameter reference values), (Continued)

c. identifying a seizure when the time course of the parameter values exhibits a characteristic of the time course of the parameter reference values (course characteristic) indicating a seizure.

14 Claims, 6 Drawing Sheets

(56)  References Cited

OTHER PUBLICATIONS

Lucia Billeci et al., "Characterizing Electrocardiogramanges During Pre-Seizure Periods Through Temporal and Spectral Features" Computing in Cardiology, 2017, vol. 44, pp. 1-4 (4 pages total).
Athi Ponnusamy et al., "Comparison of heart rate variability parameters during complex partial seizures and psychogenic nonepileptic seizures", Epilepsia, 2012, vol. 53, No. 8, pp. 1314-1321 (8 pages total).

* cited by examiner

METHOD FOR DETECTING EPILEPTIC AND PSYCHOGENIC SEIZURES

CROSS REFERENCE TO RELATED APPLICATIONS

This Application is a National Stage of International Application No. PCT/EP2020/074128, filed Aug. 28, 2020, claiming priority based on European Patent Application No. 19194188.9, filed Aug. 28, 2019.

The invention relates to a method for detecting epileptic or psychogenic seizures, in which a large number of temporally sequential parameter values are recorded and the parameter values are determined on the basis of a series of temporally sequential RR intervals. The invention also relates to a data processing device comprising means for executing the method. In addition, the invention relates to a system for detecting epileptic or psychogenic seizures that in particular is configured as a portable and mobile apparatus and includes the data processing device.

Methods are known in which for example the heart rate variability or the modified cardiac sympathetic index serve as a parameter and a time course of the values for the parameter is recorded. Furthermore, a threshold value is specified, which if exceeded means that the identification of a seizure is assumed. What is problematic is that this "threshold value approach" is patient-dependent, which means that there is no such thing as a generally applicable threshold value. This commonly results in seizures being supposedly identified even though a seizure has not actually occurred. Conversely, what also happens is that a seizure occurs but the parameter values are below the threshold value, as a result of which identification is not possible. Focal epileptic seizures in particular are currently detected only inadequately, even though this type of seizure accounts for a large proportion of epileptic seizures. In order to be able reliably to identify a seizure and to document important information about the seizure, such as the seizure type, patients have up to now been largely reliant on medical surveillance in a hospital.

The object of the invention is to propose a method for detecting epileptic and psychogenic seizures that has high reliability without the patient needing to be subjected to medical surveillance.

The object is achieved by the method according to claim 1. The object is further achieved by the device according to claim 11 and the system according to claim 12. Advantageous embodiments are described in the respective dependent claims and the description and in the figures.

According to the invention, the method comprises the following steps
   a. recording a large number of temporally sequential parameter values for a parameter type, wherein a parameter value is determined on the basis of a series of temporally sequential RR intervals, the series of temporally sequential parameter values preferably differing in that the series that served as the basis for determining the following parameter value includes, in place of the oldest RR interval of the series that served as the basis for determining the preceding parameter value (preceding series), the RR interval temporally subsequent to the most recent RR interval of the preceding series,
   b. comparing the time course of the parameter values with the time course of parameter values for the same parameter type that had been determined according to method step a, and the determination thereof is based on RR intervals that indicate a seizure (parameter reference values),
   c. identifying a seizure when the time course of the parameter values exhibits a characteristic of the time course of the parameter reference values (course characteristic) indicating a seizure.

A brief description of the drawings is as follows.

A RR interval is preferably determined by recording two consecutive R waves of an electrocardiogram using the Pan-Tompkins algorithm and then calculating the separation between the R waves. The RR interval is generally determined immediately after recording the R waves.

RR intervals indicating a seizure are RR intervals that had been determined at the time of a seizure in a patient who had suffered the seizure (seizure-indicating RR intervals). "At the time of a seizure" in this context means the time period from the onset of the seizure to the end of the seizure or a part-period of said time period. It is advantageous to also include time periods before and after the seizure, when they may have relevance to further information about a seizure, such as being able to offer conclusions about an impending seizure. Seizure-indicating RR intervals may for example have been measured during medical surveillance of the patient. The determination of the parameter reference values is advantageously based on typical seizure-indicating RR intervals, which may be determined on the basis of a large number of seizure-indicating RR intervals. Analysis of the large number of seizure-indicating RR intervals can also allow seizure-indicating RR intervals to be identified that are not only generally typical, but also specifically typical for a seizure. "Specifically typical" in this context means that the RR intervals concerned not only can be generally assigned to a seizure, but in addition also permit specific assignment to further information. Such information may for example be the type of seizure. Thus, it is not only possible to identify a seizure, but also the type of seizure.

Seizure-indicating RR intervals should strictly speaking be understood as meaning RR intervals that had been determined at the time of a seizure in a patient who had suffered the seizure (original seizure-indicating RR intervals). In a broader sense, the term "seizure-indicating RR interval" includes also RR intervals derived from original seizure-indicating RR intervals (derived seizure-indicating RR intervals). This can be done for example through machine learning. For instance, a computer could for example generate more precise and more reliable seizure-indicating RR intervals based on a steadily growing data set of seizure-indicating RR intervals.

A parameter value is determined on the basis of a series of temporally sequential RR intervals. The manner in which the RR intervals define the determination of the parameter value depends on the type of operation for which the operands are the RR intervals. The operation type may for example be calculation of the mean value. In this case, the sum of the RR intervals is calculated and divided by the number of RR intervals. The parameter value is then the mean value of the RR intervals.

For the purposes of the present invention, "temporally sequential" is generally understood to mean immediately one after the other in time.

The series of temporally sequential parameter values differ in that the series that served as the basis for determining the following parameter value (following series) includes, in place of the oldest RR interval of the series (old interval) that served as the basis for determining the preceding parameter value (preceding series), the RR interval temporally subsequent to the most recent RR interval of the preceding series (new interval). Embodiments are also conceivable in which the following series differs from the preceding series in that the following series includes, in place of a plurality of old intervals, a plurality of new intervals, the number of old intervals and the number of new intervals preferably being identical. It is preferable that each series comprises the same number of RR intervals, e.g. 100 RR intervals. It is also conceivable for each series to comprise a number of RR intervals that are measured during a defined time interval. The time interval may for example be 30 seconds.

In an alternative embodiment, the following series does not include any RR interval of the preceding series. It is conceivable for the following series to begin with the RR interval that follows temporally the most recent RR interval of the preceding series. For the purposes of the invention, "identification of a seizure" encompasses not only the eventuality that a seizure is identified once it has already commenced, but also the eventuality that a seizure has not yet commenced, but its onset is imminent. The method of the invention is therefore also suitable for warning of an impending seizure.

For the purposes of the invention, "large number" means a number of at least two. Preferably, "large number" indicates a number much greater than two, for example at least 1000.

The time course of the parameter reference values includes the course characteristic. It is however also conceivable for the time course of the parameter reference values to consist exclusively of the course characteristic or of a part thereof.

In a preferred embodiment, the method of the invention further includes the following steps
  d. recording a large number of temporally sequential parameter values for a second parameter type (second-parameter values) in accordance with method step a,
  e. comparing the time course of the values for the second parameter with the time course of parameter values for the second parameter type that had been determined in accordance with method step a, and the determination thereof is based on RR intervals that indicate a seizure (second-parameter reference values), a seizure according to method step c. being identified only when the time course of the values for the second parameter additionally exhibits a characteristic of the time course of the second-parameter reference values (course characteristic for second-parameter values) indicating a seizure.

The series that served as the basis for determining the values for the first parameter and the series that served as the basis for determining the values for the second parameter are preferably identical. In an alternative preferred embodiment, the series that served as the basis for determining the values for the first parameter and the series that served as the basis for determining the values for the second parameter are nonidentical or identical only in part. The values for the first parameter and the values for the second parameter are particularly preferably determined at the same time. It should at this point be noted that the letters designating the method steps in the claims do not place the method steps in chronological order, but merely provide a simplified means of referring to individual method steps without needing to repeat the wording of the method step to which reference is being made. However, in one conceivable embodiment, the alphabetic sequence of the letters places the method steps in the claims in chronological order.

The embodiment according to claim 2 in particular has the advantage that the probability of a seizure being detected in error is reduced, and a seizure is detected only when two conditions are cumulatively met: The time course of the parameter values for the first parameter exhibits a course characteristic and the time course of the values for the second parameter exhibits a course characteristic for second-parameter values.

In an alternative embodiment of the invention, the method for detecting an epileptic or psychogenic seizure comprises the following steps
  recording a large number of temporally sequential parameter values for a parameter type, wherein a parameter value is determined on the basis of a series of temporally sequential RR intervals, the series of temporally sequential parameter values preferably differing in that the series that served as the basis for determining the following parameter value includes, in place of the oldest RR interval of the series that served as the basis for determining the preceding parameter value (preceding series), the RR interval temporally subsequent to the most recent RR interval of the preceding series,
  recording a large number of temporally sequential parameter values for an at least second parameter type (values for the second parameter) in accordance with the preceding method step of this alternative embodiment,
  comparing the time course of the values for the first parameter with the time course of values for the second parameter,
  determining on the basis of the comparison whether or not a seizure is present.

This alternative embodiment differs from the other embodiments in that no parameter reference values and reference characteristics are needed for identification of a seizure.

In a preferred embodiment, the method of the invention further includes the following steps
  f. performing steps d. and e. in an analogous manner for at least a third parameter type,
  a seizure according to method step c. being identified only when the time course of the values for the third parameter additionally exhibits a characteristic of the time course of the third-parameter reference values (course characteristic for third-parameter values) indicating a seizure.

The term "at least" indicates that method step f. may be executed in an analogous manner for any desired number of parameter types. Thus it is possible, for example, for there to be in addition to a third parameter also a fourth parameter, i.e. a parameter value for a fourth parameter type. Thus, the condition of this embodiment can likewise be applied in an analogous manner to a fourth parameter. In this eventuality, the condition would read: "[ . . . ] when the time course of the values for the fourth parameter additionally exhibits a characteristic of the time course of the fourth parameter reference values (course characteristic for fourth-parameter values) indicating a seizure."

The second parameter type is a different parameter type than the (first) parameter type. The third parameter type is one different than the second parameter type and one different than the (first) parameter type. The same applies to any further parameter types. Thus, a fourth parameter type is for example one different than the first, second and third parameter type.

The series that served as the basis for determining the values for the first parameter, the series that served as the basis for determining the values for the second parameter and the series that served as the basis for determining the values for the third parameter are preferably identical. It is however also perfectly conceivable for the series that served as the basis for determining the values for the first parameter, and the series that served as the basis for determining the values for the second parameter and the series that served as the basis for determining the values for the third parameter, etc., to be nonidentical or identical only in part. The values for the first parameter, the values for the second parameter and the values for the third parameter are particularly preferably determined at the same time.

In an alternative embodiment of this embodiment, the method of the invention further includes the following method steps
performing steps d. and e. in an analogous manner for at least a third parameter type,
a seizure according to method step c. being identified when the time course of the values for the third parameter does not exhibit a course characteristic for third-parameter values.

In a preferred embodiment, the parameter type is the mean value, the standard deviation, the cardiac sympathetic index (CSI), the functionally modified cardiac sympathetic index (CSImod), the cardiovascular index, the Baevsky stress index, the adequacy index of regulatory processes, the vegetative equilibrium index, the vegetative rhythm index, the square root of the mean of the sum of all squared differences between successive RR intervals (RMSSD), the skewness of the distribution of the RR intervals (RRSkew), the kurtosis of the distribution of the RR intervals (RRKurt), the percentage of intervals differing by at least 50 milliseconds from the preceding interval (pNN50), the number of pairs of successive RR intervals that throughout the recording differ from one another by more than 50 milliseconds (NN50), the frequency range below 0.003 hertz (ULF), the 0.003 to 0.04 hertz frequency range (VLF), the 0.04 to 0.15 hertz frequency range (LF), the 0.14 to 0.4 hertz frequency range (HF), the ratio of LF to HF, the absolute spectral power density (ttlpwr), the most strongly represented spectral power density from the low-frequency band and from the high-frequency band, the most strongly occurring frequency in the low- and high-frequency band, the acceleration and deceleration capacity of the cardiac rhythm based on RR intervals (PRSA-AC and PRSA-DC), the sample entropy (SampEn), the approximate entropy (ApEn), the coefficient of sample entropy (CoSEN), the long-term and short-term detrended fluctuation analysis (DFA), the integral of the density distribution or the triangular index (TRI), the approximate length and width of the ellipse of the Poincaré plot and ratio thereof, the heart rate turbulence (HRT) or the recurrence rate (REC).

The time course of the parameter values can be visualized for example when the parameter values are plotted against time in a coordinate system. The course characteristic can thereby also be visualized. This may have a particular shape. In a preferred embodiment, the course characteristic is an essentially linearly descending curve (linear descent) when the parameter type is the mean value, and an essentially hill-shaped curve (hill shape) when the parameter type is the standard deviation or the CSI.

In a preferred embodiment, the parameter type of the (first) parameter values is the mean value, the parameter type of the second parameter values is the standard deviation and the parameter type of the third parameter values is the CSI.

In a preferred embodiment of the method of the invention, the method further includes the following steps
forming temporally sequential intervals that comprise temporally sequential parameter values (parameter intervals), parameter intervals being temporally sequential such that a following parameter interval differs from the preceding parameter interval in that it includes, in place of the oldest parameter value of the preceding parameter interval, the parameter value temporally subsequent to the most recent parameter value of the preceding parameter interval,
examining the parameter intervals one at a time to see whether the course characteristic occurs in the individual parameter interval.

Parameter intervals follow one another temporally such that a following parameter interval differs from the preceding parameter interval in that it includes, in place of the oldest parameter value of the preceding parameter interval (old parameter value), the parameter value temporally subsequent to the most recent parameter value of the preceding parameter interval (new parameter value). Embodiments are also conceivable in which the following parameter interval differs from the preceding parameter interval in that the following parameter interval includes, in place of a plurality of old parameter values, a plurality of new parameter values, the number of old parameter values and the number of new parameter values preferably being identical. It is preferable that each parameter interval comprises the same number of parameter values.

In a preferred embodiment of the method of the invention, the method includes the following method steps:
subdividing the parameter intervals into at least two sub-intervals preferably of essentially equal size
determining a supra-parameter value for each sub-interval
identifying on the basis of the supra-parameter values whether or not a course characteristic is present.

A supra-parameter value is determined on the basis of a series of temporally sequential parameter values. The manner in which the parameter values define the determination of the supra-parameter value depends on the type of operation for which the operands are the parameter values. The operation type may for example be calculation of the mean value. In this case, the sum of the parameter values is calculated and divided by the number of parameter values. The supra-parameter value is then the mean value of the parameter values. The supra-parameter value accordingly corresponds to the parameter value. The supra-parameter value is preferably one of the examples of parameter values cited in the application (e.g. mean value, CSImod, REC, etc.).

In a preferred embodiment of the method of the invention, the method further includes the following steps
- subdividing the parameter intervals into preferably four sub-intervals of essentially equal size
- determining the mean of all the parameter values of each sub-interval
- identifying the course characteristic "linearly descending" when the mean value of each older sub-interval is greater than the mean value of each more recent sub-interval.

The size of a sub-interval is defined by the number of parameter values that the sub-interval comprises. For the purposes of the invention, "sub-intervals of essentially equal size" means that the sub-intervals are of equal size or that any difference in size does not adversely affect the identification of the course characteristic. In the case of the latter alternative, the ratio between sub-interval size and average interval size can be used as an evaluation criterion. This is to be elucidated by one example: The sub-intervals are 101, 99, 102 and 98 parameter values in size. The average interval size is 100 parameter values. The sub-intervals differ from the average interval size only by 1 to 2% based on this. This is an indication that the sub-intervals are in accordance with the invention of essentially equal size.

The method of this embodiment may be executed multiple times, wherein the number of RR intervals included in a series (series length) varies each time it is executed. These multiple executions may take place at the same time or successively. Preferably, the number of executions is three, the series length being 50, 75, 100 RR intervals. The result for each execution is the identification or non-identification of a course characteristic. The results of the executions can be linked into logical statements using Boolean algebra. It can for example be defined that, as the overall result, a course characteristic is present when one of the executions produces the result that a course characteristic has been identified.

Alternatively, a different number of sub-intervals is also conceivable.

In a further preferred embodiment of this embodiment of the method of the invention, the method further includes the following steps
- subdividing the parameter intervals into four sub-intervals of essentially equal size,
- determining the mean of all the parameter values of each sub-interval
- subdividing the oldest sub-interval into four sub-intervals of equal size (sub-sub-intervals) and determining the mean of all the parameter values of each sub-sub-interval,
- for the oldest sub-interval, examining whether the mean value for each more recent sub-sub-interval is greater than the mean value for each older sub-sub-interval (linear ascent in the oldest sub-sub-interval),
- subdividing the most recent sub-interval into four sub-intervals of equal size (sub-sub-intervals) and determining the mean of all the parameter values of each sub-sub-interval,
- for the most recent sub-interval, examining whether the mean value for each older sub-sub-interval is greater than the mean value for each more recent sub-sub-interval (linear descent in the most recent sub-sub-interval),
- identifying the course characteristic "hill shape" when
  - the oldest sub-sub-interval exhibits a linear ascent,
  - the most recent sub-sub-interval exhibits a linear descent,
  - the mean value of the oldest sub-interval is smaller than the mean value of the second-oldest sub-interval and
  - the mean value of the second-most recent sub-interval is greater than the mean value of the most recent sub-interval.

The method of this embodiment may be executed multiple times, wherein the number of RR intervals included in a series (series length) varies each time it is executed. These multiple executions may take place at the same time or successively. Preferably, the number of executions is four, the series length being 50, 75, 100 and 150 RR intervals. The result for each execution is the identification or non-identification of a course characteristic. The results of the executions can be linked into logical statements using Boolean algebra. It can for example be defined that, as the overall result, a course characteristic is present when one of the executions produces the result that a course characteristic has been identified.

The method of the invention is suitable for the surveillance of a patient such that a prompt alert can be issued as soon as a seizure has been identified. In this situation it is advisable that the method steps are executed immediately and swiftly after the determination of the RR intervals. For a prompt alert it is therefore favourable when the series comprise a relatively small number of RR intervals. In an advantageous embodiment, a series comprises 4 to 300 RR intervals.

The method of the invention is also suitable for the analysis of seizures. In this case it is also possible to use RR intervals that had been determined a relatively long time ago. With the aid of the method of the invention it is then possible not only to establish whether and how often the patient had suffered a seizure in the past, but to identify the type of seizure too. For analysis purposes it is therefore advantageous when the series comprise a relatively large number of RR intervals. In a preferred embodiment, a series comprises 4 to 5000 RR intervals.

In a preferred embodiment, the method includes the following method steps:
- forming temporally sequential intervals that comprise temporally sequential parameter values (parameter intervals), parameter intervals being temporally sequential such that a following parameter interval differs from the preceding parameter interval in that it includes, in place of the oldest parameter value of the preceding parameter interval, the parameter value temporally subsequent to the most recent parameter value of the preceding parameter interval,
- classifying at least one parameter interval according to whether it indicates or does not indicate a seizure, wherein the classification is executed by means of an artificial neural network, the network having an input layer, preferably at least one intermediate layer, and an output layer, the input layer comprising the parameter interval such that neurons of the input layer each represent one parameter value of the parameter interval, the output layer comprising at least one neuron, the neuron of the output layer representing the result of the classification whether the parameter interval does or does not indicate a seizure.

Artificial neural networks are known. Typically, each neuron of the input layer is linked to each neuron of the intermediate layer. Typically, each neuron of the intermediate layer is also linked to each neuron of the output layer.

The output layer preferably comprises a single neuron. The network is preferably feedforward, i.e. neurons of one layer are controlled by the neurons of the preceding layer. For example, the neurons of the input layer control the neurons of the intermediate layer and the neurons of the intermediate layer control the neurons of the output layer. This usually takes place in that the values of the neurons of the preceding layer that are connected to a neuron of the following layer are multiplied by their respective weight and the sum of the thus weighted values is transmitted to an activation function as a so-called network input. The activation function assigns to each network input an output that is transmitted to the corresponding neuron of the following layer. Here, a threshold value can be specified that ensures that the output is transmitted to the neuron of the following layer only when it is above a certain value. One or more bias neurons may also be provided.

The network preferably has a large number of intermediate layers (deep learning).

The neurons of the input layer each represent one parameter value of the parameter interval. The representation usually takes the form of a numerical value. The parameter interval may for example have a plurality of parameter values for the parameter type "mean value". It thus comprises a plurality of mean values. The numerical value through which the representation occurs is in this case one of the plurality of mean values. This is to be illustrated by one example: A parameter interval comprises three parameter values for the parameter type "mean value". The oldest parameter value is the mean value 5, the second-oldest parameter value is the mean value 3 and the most recent parameter value is the mean value 9. In addition, an input layer having three neurons would in this example be provided. The first neuron, which represents the oldest parameter value, would have the numerical value 5. The second neuron, which represents the second-oldest parameter value, would have the numerical value 3. Lastly, the third neuron, which represents the most recent parameter value, would have the numerical value 9. The neurons in the input layer are preferably arranged in a series, wherein the first neuron in the series represents the oldest parameter value, the second neuron in the series represents the second-oldest parameter value and so on. The input layer preferably comprises 55 or 128 neurons.

A classification of at least one parameter interval is carried out. Preferably, a classification of a plurality of parameter intervals is carried out. The classification of the parameter intervals may be executed in a stepwise manner from the classification of the oldest parameter interval to the most recent parameter interval. It is also possible for all parameter intervals to undergo classification at the same time.

In the preferred embodiment in which a plurality of parameter intervals undergoes classification at the same time, the input is preferably considered as a (two-dimensional) matrix.

In a preferred embodiment, the method further includes the following method steps forming temporally sequential intervals that comprise temporally sequential second-parameter values (second-parameter intervals), second-parameter intervals being temporally sequential such that a subsequent second-parameter interval differs from the preceding second-parameter interval in that it includes, in place of the oldest second-parameter value of the preceding second-parameter interval, the second-parameter value temporally subsequent to the most recent second-parameter value of the preceding second-parameter interval, classifying at least one second-parameter interval according to whether it indicates or does not indicate a seizure, wherein the classification is executed by means of the artificial neural network, the input layer comprising the second-parameter interval such that neurons of the input layer that are designated for the second-parameter interval (second neurons) each represent one second-parameter value of the second-parameter interval, the output layer comprising at least one neuron representing the result of the classification whether the second-parameter interval does or does not indicate a seizure, wherein the series of temporally sequential RR intervals that served as the basis for determining the parameter values of the parameter interval and the series of temporally sequential RR intervals that served as the basis for determining the second-parameter values of the second-parameter interval are identical or partially identical, the classification of the parameter interval and the classification of the second-parameter interval preferably being executed at the same time. The classification can thus be executed for parameter intervals having parameter values of different parameter types where these are (at least in part) based on the same RR intervals. They consequently relate (at least in part) to the same period. When based on the same RR intervals, the parameter interval for the first parameter and the parameter interval for the second parameter lead to a common result, thus either that a seizure is present or absent.

The neural network preferably has only one output neuron, even in the variant with a plurality of parameter intervals of different parameter types.

This embodiment has the advantage that the neural network becomes trained such that it also makes use of connections between the parameter intervals of different parameter types for the classification. It can for example make use of the finding that a seizure is present when for example the parameter interval for the parameter type "mean value" has a linear course while the parameter interval for the second parameter for the second-parameter type "standard deviation" has a hill shape. This is merely a simple example intended to give an impression of how connections between the parameter intervals of different parameter types can be detected by the neural network and how these findings can lead to a more reliable classification.

Particularly preferably, the method additionally includes the formation of parameter intervals for a third parameter and the classification of at least one parameter interval for a third parameter, this being done in an analogous manner to the described procedure for the parameter intervals for the first and second parameters. The higher the number of parameter intervals for different parameter type (parameter intervals for a first, second, third and fourth parameter), the more reliable the classification can be. For example, the number of parameter intervals for different parameter type can be 36.

In a preferred embodiment, the network has been trained with a data set of parameter intervals, this having been done using the supervised learning method, the data set comprising parameter intervals indicating a seizure (seizure parameter intervals) and parameter intervals not indicating a seizure (non-seizure parameter intervals), wherein at least one seizure parameter interval of the input layer has been transmitted such that neurons of the input layer each represent one parameter value of the seizure parameter interval, network parameters having been tuned with the aim of increasing the reliability of the classification if the network has erroneously classified the seizure parameter interval as a non-seizure parameter interval, network parameters having remained unchanged if the network has correctly classified the seizure parameter interval as a seizure parameter interval, wherein at least one non-seizure parameter interval of the input layer has been transmitted such that neurons of the input layer each represent one parameter value of the non-seizure parameter interval, network parameters having been tuned with the aim of increasing the reliability of the classification if the network has erroneously classified the non-seizure parameter interval as a seizure parameter interval, network parameters having remained unchanged if the network has correctly classified the non-seizure parameter interval as a non-seizure parameter interval.

The invention also relates to the training of an artificial neural network to classify at least one parameter interval, wherein the network is trained with a data set of parameter intervals, this being done using the supervised learning method, the data set comprising parameter intervals indicating a seizure (seizure parameter intervals) and parameter intervals not indicating a seizure (non-seizure parameter intervals), wherein at least one seizure parameter interval of the input layer is transmitted such that neurons of the input layer each represent one parameter value of the seizure parameter interval, network parameters being tuned with the aim of increasing the reliability of the classification if the network erroneously classifies the seizure parameter interval as a non-seizure parameter interval, network parameters remaining unchanged if the network correctly classifies the seizure parameter interval as a seizure parameter interval, wherein at least one non-seizure parameter interval of the input layer is transmitted such that neurons of the input layer each represent one parameter value of the non-seizure parameter interval, network parameters being tuned with the aim of increasing the reliability of the classification if the network erroneously classifies the non-seizure parameter interval as a seizure parameter interval, network parameters remaining unchanged if the network correctly classifies the non-seizure parameter interval as a non-seizure parameter interval.

A network parameter is for example a weight of a neuron. Particularly preferably, the weight of a plurality of neurons undergoes tuning. These are preferably (the) neurons of the at least one intermediate layer and/or neurons of the output layer. Further examples of network parameters are bias neurons.

The training is preferably followed by a test phase in which parameter intervals of the data set and/or new parameter intervals are used to test whether parameter intervals are being reliably classified by the network.

The invention also relates to a data processing device that has means for executing the method of the invention. The data processing device may be for example a computer or a smartphone.

The invention further relates to a system for detecting epileptic or psychogenic seizures that includes the data processing device of the invention. This system further includes a sensor for recording heartbeat data and also an output unit for communicating information about the detection. Through the sensor for recording heartbeat data, it is possible to determine RR intervals through direct measurement on the patient. This allows the system to be used for monitoring a patient at risk of seizures. The output unit communicates to the user (e.g. the patient or a doctor) information about a detected seizure, for example the occurrence of a seizure, the seizure type and the time of the seizure. This can trigger an alarm, for example. It is however also possible for information to be saved in a seizure diary. The save location of the seizure diary may for example be in the data processing device.

In a preferred embodiment of the system of the invention, the system further includes a transmitter for transmitting information about the detection. The transmitter is used for example to send an emergency call or alarm when a seizure has been detected.

In a preferred embodiment, the system is designed as a portable and mobile apparatus. The portable and mobile design of the apparatus can be modelled for example on a mobile ECG device. The apparatus may be attached for example to the patient's wrist or chest. This allows the patient to be reliably monitored even without a doctor being present and without it being associated with a hospital admission.

The invention is explained hereinbelow with reference to exemplary embodiments.

Figure 1:
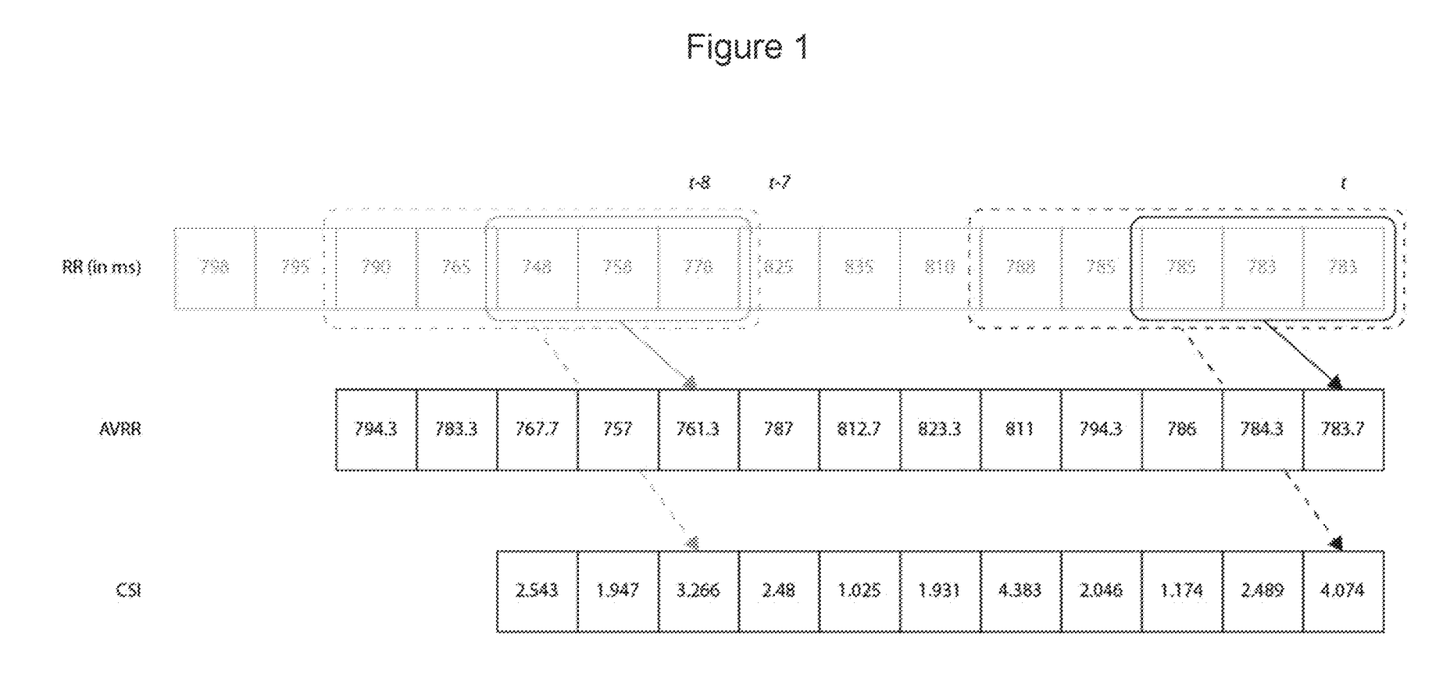
FIG. 1 is an illustration of how temporally sequential parameter values are determined.

FIG. 1 illustrates how temporally sequential parameter values are determined. Three rows can be seen, a top row, a middle row and a bottom row. The top row is populated with the RR intervals that have actually been determined. These may for example be RR intervals measured in a patient at risk of seizures in order to monitor whether the patient is suffering a seizure or a seizure is imminent. The example depicted in FIG. 1 shows 15 RR intervals (15 boxes). Shown in each box is the respective value of the corresponding RR interval in units of milliseconds (ms). For example, the first RR interval has the value 798 ms and the second interval the value 795 ms. The RR intervals shown are temporally sequential. In this row, the RR interval at the extreme left (798 ms) is the oldest in time of the RR intervals shown (i.e. the first one measured) and the RR interval at the extreme right (783 ms) the most recent (i.e. the last one measured). The middle row is populated with the parameter values for the parameter type "mean value". At time t, i.e. the time at which the most recent RR interval had been measured, the mean value based on the last series of temporally sequential RR intervals has the value 783.7. The series here comprises, for illustration purposes, a length of 3 RR intervals. The mean value 783.7 is thus the mean value of the three most recent RR intervals 785, 783 and 783. In the last row, the parameter type CSI for the same time t has for illustration purposes the value 4.074, determined on the basis of the five most recent RR intervals (788, 785, 785, 783 and 783). The series that served as the basis for determining the second parameter (in this case CSI) has five RR intervals and is thus larger than the series that served as the basis for determining the (first) parameter (mean value), which comprises only three RR intervals. The series length for the different parameters is in this example different.

The mean value at time t−8 (the RR interval here has the value 778 ms and the mean value is 761.3 ms) is likewise determined on the basis of a series of three RR intervals, namely 748, 758 and 778 (these are shown inside the rectangle bordered with solid lines). The series for determining each mean value (middle row) is thus in FIG. 1 three RR intervals in length. The series that served as the basis for determining the mean value at t−8 is the preceding series for the series that served as the basis for determining the mean value at t−7, which is in turn the following series of this preceding series. This following series comprises the RR intervals 758, 778 and 825. The series, which in the present example has a constant length of three RR intervals, thus moves from left to right, figuratively speaking one box at a time. This continues in the present example until the last row that is visible in FIG. 1 is reached (RR intervals 785, 783 and 783).

The values for the CSI are likewise determined according to this "moving series" principle. For example, the CSI has at time t–8 the value 3.266, which is determined on the basis of the five RR intervals shown inside the rectangle bordered with dashed lines (RR intervals 790, 765, 748, 758, 778). The series serving as the basis for determining the second parameter CSI is in this example likewise always of constant length (but with the length of 5, unlike the first parameter). This series too moves to the right one box at a time until reaching the last row that is visible, which consists of the RR intervals 788, 785, 785, 783, 783. With each step further that it moves, a CSI value is determined (see bottom row).

Figure 2:
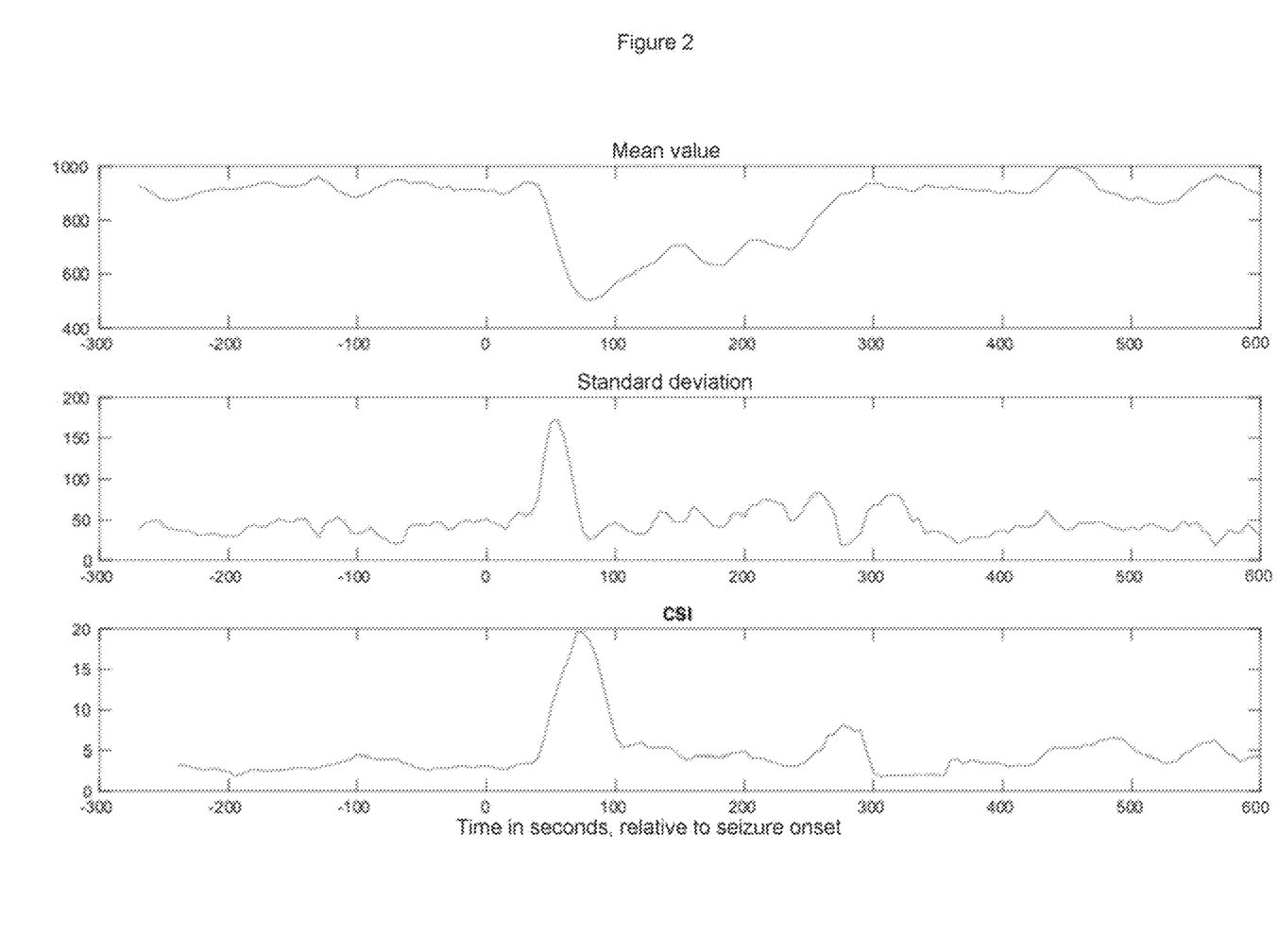
FIG. 2 is a set of graphs showing the time course of a large number of temporally sequential parameter values for a first parameter type (top graph), the time course of a large number of temporally sequential parameter values for a second parameter type (middle graph) and the time course of a large number of temporally sequential parameter values for a third parameter type (bottom graph)

FIG. 2 shows the time course of a large number of temporally sequential parameter values for a first parameter type (top graph), the time course of a large number of temporally sequential parameter values for a second parameter type (middle graph) and the time course of a large number of temporally sequential parameter values for a third parameter type (bottom graph). The first parameter type is the mean value, the second parameter type is the standard deviation and the third parameter type is the CSI. The course characteristics are clearly visible, all of them being located at a time of about 40 seconds. The RR intervals recorded at this time indicate a seizure. All three graphs are in agreement in exhibiting a course characteristic at this point. The course characteristic of the parameter values for the parameter type "mean value" (top) is a linear descent, whereas the course characteristic of the parameter values of the parameter type "standard deviation" (middle) and of the parameter type "CSI" (bottom) is a hill shape.

Figure 3:
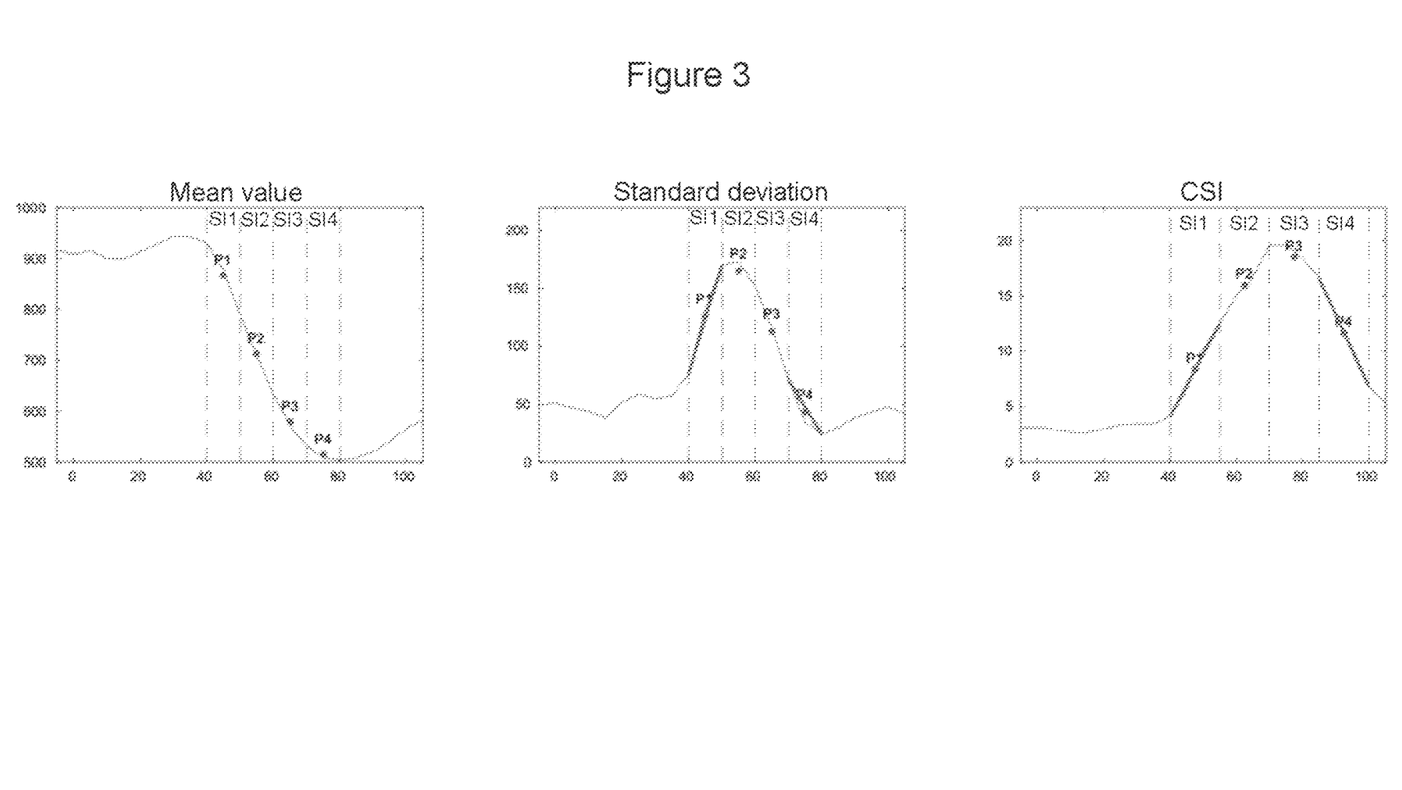
FIG. 3 is a set of graphs illustrating the subdivision of the parameter intervals into four sub-intervals (SI1, SI2, SI3, SI4) for the parameter values of three parameter types (left sub-figure: mean value; middle sub-figure: standard deviation; right sub-figure: CSI)

FIG. 3 illustrates the subdivision of the parameter intervals into four sub-intervals (SI1, SI2, SI3, SI4) for the parameter values of three parameter types (left sub-figure: mean value; middle sub-figure: standard deviation; right sub-figure: CSI). On the basis of the four subintervals, taking the parameter type "mean value" as an example, all mean values of the parameter values of each subinterval are determined (P1, P2, P3, P4). (For better understanding, it should be noted that the parameter interval in this example runs from 40 to 80 seconds.) The identification of the course characteristic "linear descent" is possible on this basis when the mean value of each older subinterval is greater than the mean value of each more recent subinterval, as shown in the left sub-figure (graph for mean value). For the parameter types "standard deviation" (middle sub-figure) and "CSI" (right sub-figure), the course characteristic "hill shape" is identified as follows: subdivision into four sub-intervals of essentially equal size and examination whether the oldest sub-interval (SI1) exhibits the course characteristic "linear ascent", whether the most recent sub-interval (SI4) exhibits the course characteristic "linear descent", whether the mean value for the oldest sub-interval (SI1) is smaller than the mean value for the second-oldest sub-interval (SI2) and the mean value for the second-most recent sub-interval (SI3) is smaller than the mean value for the most recent sub-interval (SI4). The determination of the course characteristic "linear ascent" in the oldest sub-interval (SI1) is done by subdividing the sub-interval into four sub-sub intervals of equal size (not shown); for each sub-sub interval the mean value is determined and the course characteristic "linear ascent" is identified when the mean value of each older sub-sub-interval is smaller than the mean value of each more recent sub-sub-interval. The same applies to the determination of the course characteristic "linear descent" for the most recent sub-interval (SI4). It should for the sake of completeness be noted that the parameter interval in the middle sub-figure runs from 40 to 80 seconds and that in the right sub-figure from 40 to 100. The result for each execution is the identification or non-identification of a course characteristic. The results of the executions can be linked into logical statements using Boolean algebra (FIG. 4).

Figure 4:
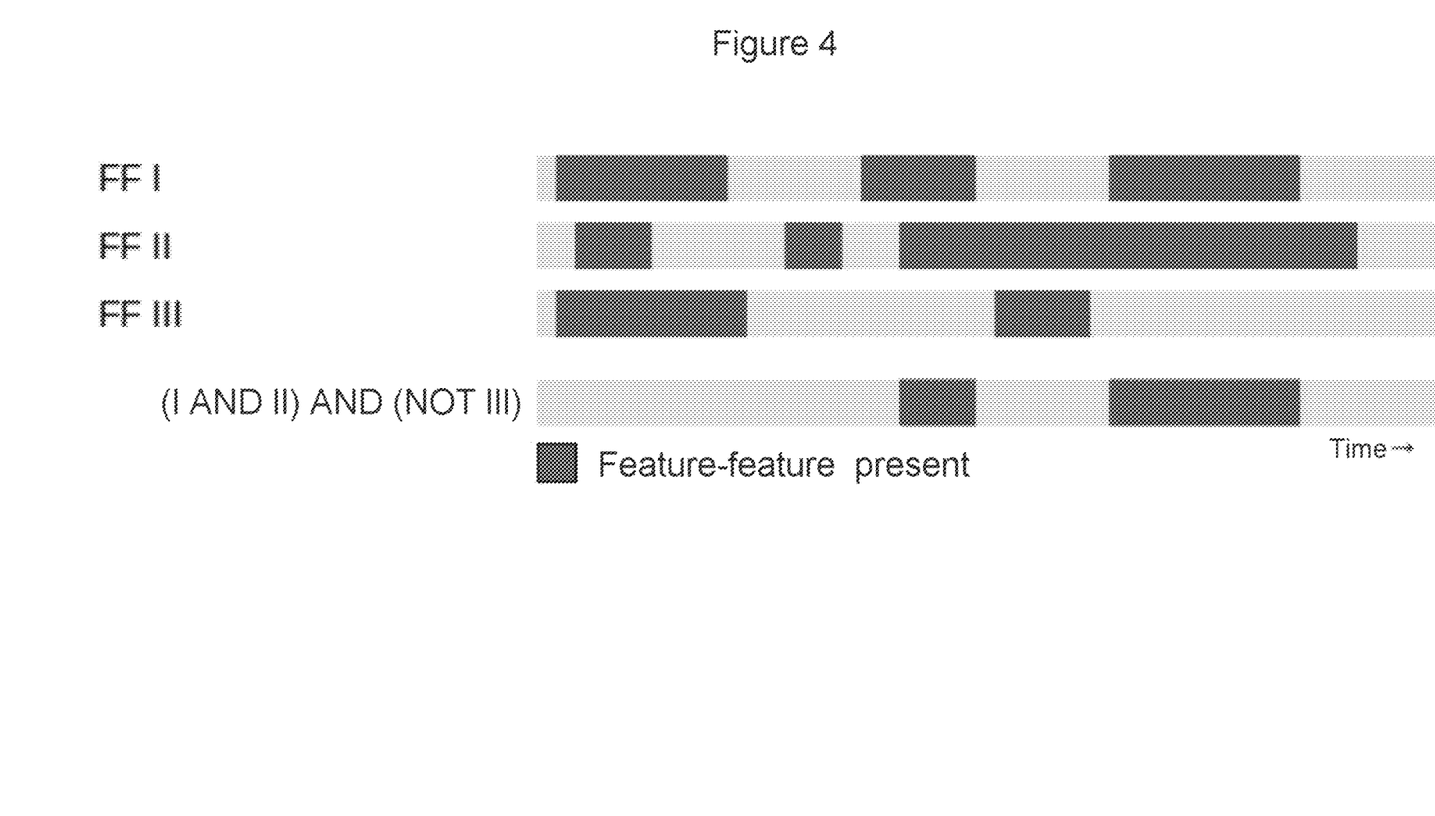
FIG. 4 shows an example of logical linking of detection results for different parameter types.

FIG. 4 shows an example of logical linking of detection results for different parameter types. In the following description, reference is first made to the topmost three rows. Each row represents the identification of a different course characteristic. For example, the top row (FF I) shows whether the course characteristic "linear descent" (parameter type "mean value") has been identified, the second row from the top (FF II) whether the course characteristic "hill" of the parameter type "standard deviation" has been identified and the third row from the top (FF III) whether the course characteristic "hill" of the parameter type "CSI" has been identified. Whether a course characteristic has been identified and over what period of time is indicated by the dark bars and the length thereof. The bottom row shows the end result: whether a seizure has occurred and over what period of time. The top three rows are linked with the bottom row via a logical operation, which in the example in FIG. 4 is as follows: Only when a course characteristic is identified in FF I and a course characteristic is identified in FF II and, in addition also, no course characteristic is identified in FF III, is a seizure identified in the bottom row.

Figure 5:
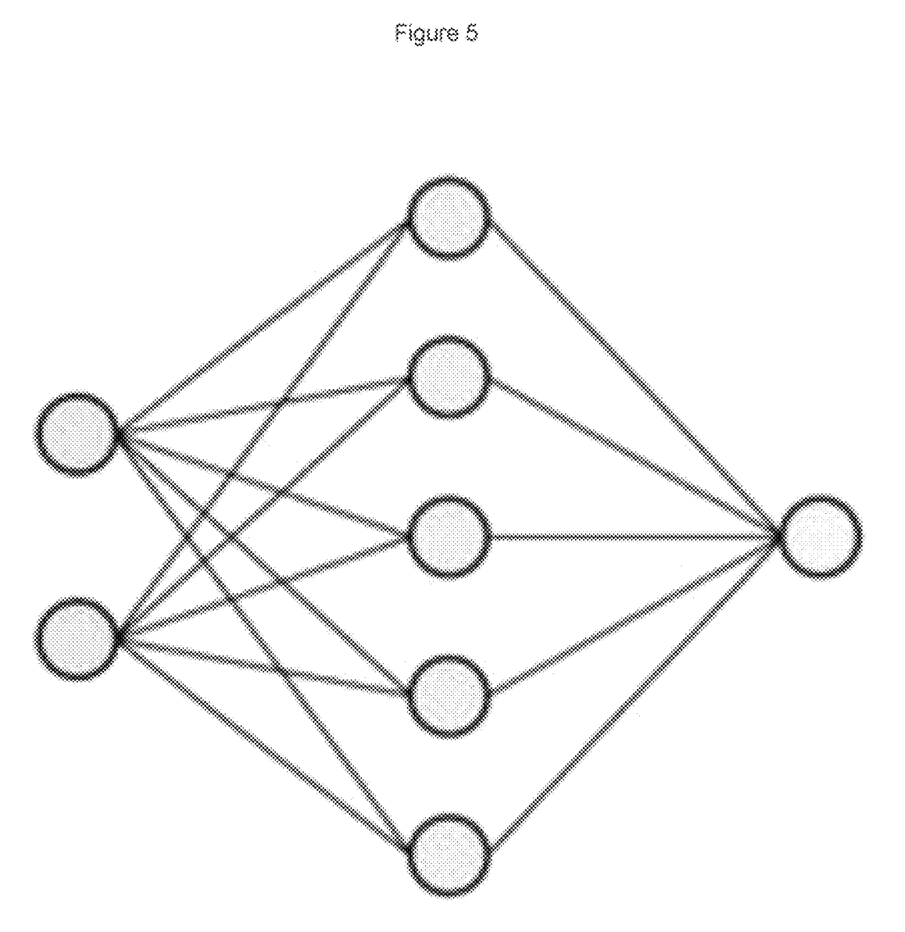
FIG. 5 shows an exemplary artificial neural network for classifying a parameter interval according to whether it indicates or does not indicate a seizure.

FIG. 5 shows an exemplary artificial neural network for classifying a parameter interval according to whether it indicates or does not indicate a seizure. The network for the sake of clarity comprises an input layer having only two neurons (left), an intermediate layer having five neurons (middle) and an output layer having one neuron (right). Each neuron of the input layer is connected to each neuron of the intermediate layer and each neuron of the intermediate layer is connected to the neuron of the output layer. The top neuron of the input layer represents the most recent parameter value of the parameter interval and the bottom neuron represents the oldest parameter value of the parameter interval. The neuron of the output layer indicates the result of the classification, i.e. whether the parameter interval exhibited by the input layer is a seizure parameter interval or a non-seizure parameter interval.

Figure 6:
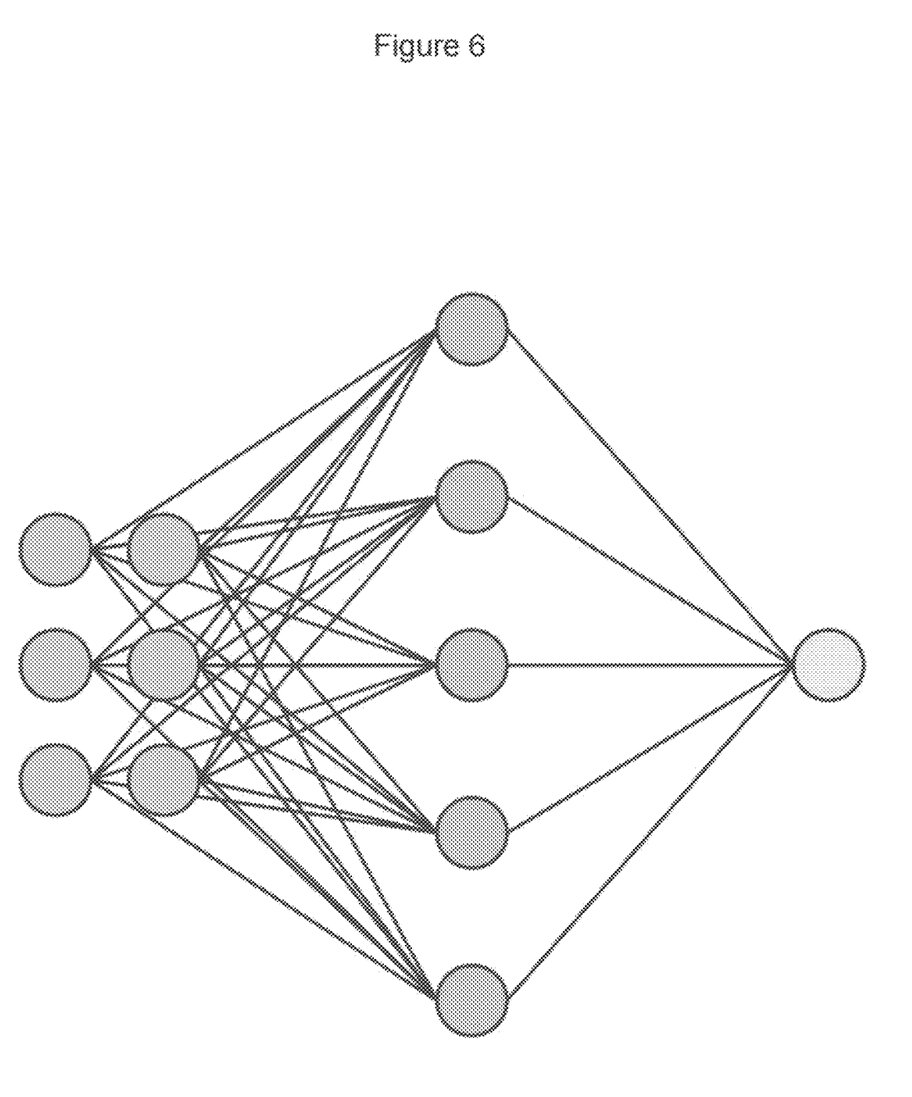
FIG. 6 shows an exemplary artificial neural network for classifying a parameter interval of one parameter type and for classifying a second-parameter interval of a second parameter type.

FIG. 6 shows an exemplary artificial neural network for classifying a parameter interval of one parameter type and for classifying a second-parameter interval of a second parameter type. The artificial neural network from FIG. 6 differs from the one shown in FIG. 5 in that the input layer has two columns, each comprising three neurons. The first column comprises the neurons of the first parameter interval and the second column comprises the second neurons, i.e. the neurons of the second-parameter interval. The first row of the input layer can include a value for a first parameter and a value for a second parameter that are based on identical or part-identical series of RR intervals. The same applies for the second and third rows.

The invention claimed is:
1. Method for detecting epileptic or psychogenic seizures, comprising the steps of:
   a. recording a large number of temporally sequential parameter values for a parameter type, wherein a parameter value is determined on the basis of a series of temporally sequential RR intervals, wherein the parameter type is a mean value, a standard deviation, a cardiac sympathetic index (CSI), a functionally modi- fied cardiac sympathetic index (CSImod), a cardiovascular index, a Baevsky stress index, an adequacy index of regulatory processes, a vegetative equilibrium index, a vegetative rhythm index, a square root of a mean of a sum of all squared differences between successive RR intervals (RMSSD), a skewness of a distribution of the RR intervals (RRSkew), a kurtosis of the distribution of the RR intervals (RRKurt), a percentage of intervals differing by at least 50 milliseconds from the preceding interval (pNN50), a number of pairs of successive RR intervals that throughout the recording differ from one another by more than 50 milliseconds (NN50), a frequency range below 0.003 hertz (ULF), a 0.003 to 0.04 hertz frequency range (VLF), a 0.04 to 0.15 hertz frequency range (LF), a 0.14 to 0.4 hertz frequency range (HF), a ratio of LF to HF, an absolute spectral power density (ttlpwr), a most strongly represented spectral power density from a low-frequency band and from a high-frequency band, a most strongly occurring frequency in the low-and high-frequency band, an acceleration and deceleration capacity of a cardiac rhythm based on RR intervals (PRSA-AC and PRSA-DC), a sample entropy (SampEn), an approximate entropy (ApEn), a coefficient of sample entropy (CoSEN), a long-term and short-term detrended fluctuation analysis (DFA), an integral of a density distribution or a triangular index (TRI), an approximate length and width of an ellipse of a Poincaré plot and ratio thereof, a heart rate turbulence (HRT) or a recurrence rate (REC), b. comparing the time course of the parameter values with the time course of parameter values for the same parameter type that had been determined according to method step a, and the determination thereof is based on RR intervals that indicate a seizure (parameter reference values), c. identifying a seizure when the time course of the parameter values exhibits a characteristic of the time course of the parameter reference values (course characteristic) indicating a seizure.

2. Method according to claim 1, comprising the following steps d. recording a large number of temporally sequential parameter values for a second parameter type (second-parameter values) in accordance with method step a, e. comparing the time course of the values for the second parameter with the time course of parameter values for the second parameter type that had been determined in accordance with method step a, and the determination thereof is based on RR intervals that indicate a seizure (second-parameter reference values), a seizure according to method step d. being identified only when the time course of the values for the second parameter additionally exhibits a characteristic of the time course of the second-parameter reference values (course characteristic for second-parameter values) indicating a seizure.

3. Method according to claim 2, additionally comprising the following steps f. performing steps d. and e. in an analogous manner for at least a third parameter type, a seizure according to method step c. being identified only when the time course of the values for the third parameter additionally exhibits a characteristic of the time course of the third-parameter reference values (course characteristic for third-parameter values) indicating a seizure or a seizure according to method step c. being identified when the time course of the values for the third parameter does not exhibit a course characteristic for third-parameter values.

4. Method according to claim 3, wherein the parameter type of the (first) parameter values is the mean value, the parameter type of the second parameter values is the standard deviation and the parameter type of the third parameter values is the CSI.

5. Method according to claim 1, wherein the parameter type is the mean value, the standard deviation, the cardiac sympathetic index (CSI), the functionally modified cardiac sympathetic index (CSImod), the cardiovascular index, the Baevsky stress index, the adequacy index of regulatory processes, the vegetative equilibrium index or the vegetative rhythm index.

6. Method according to claim 5, wherein
the course characteristic is an essentially linearly descending curve (linear descent) when the parameter type is the mean value and
the course characteristic is an essentially hill-shaped curve (hill shape) when the parameter type is the standard deviation or the CSI.

7. Method according to claim 1, comprising the following method steps:
forming temporally sequential intervals that comprise temporally sequential parameter values (parameter intervals), parameter intervals being temporally sequential such that a following parameter interval differs from the preceding parameter interval in that it includes, in place of the oldest parameter value of the preceding parameter interval, the parameter value temporally subsequent to the most recent parameter value of the preceding parameter interval,
examining the parameter intervals one at a time to see whether the course characteristic occurs in the individual parameter interval.

8. Method according to claim 1, wherein a series comprises 4 to 300 or 4 to 5000 RR intervals.

9. Method according to claim 1, the series of temporally sequential parameter values differing in that the series that served as the basis for determining the following parameter value includes, in place of the oldest RR interval of the series that served as the basis for determining the preceding parameter value (preceding series), the RR interval temporally subsequent to the most recent RR interval of the preceding series.

10. Method for detecting epileptic or psychogenic seizures, comprising the steps of:

a. recording a large number of temporally sequential parameter values for a parameter type, wherein a parameter value is determined on the basis of a series of temporally sequential RR intervals, b. comparing the time course of the parameter values with the time course of parameter values for the same parameter type that had been determined according to method step a, and the determination thereof is based on RR intervals that indicate a seizure (parameter reference values), c. identifying a seizure when the time course of the parameter values exhibits a characteristic of the time course of the parameter reference values (course characteristic) indicating a seizure, further comprising the following method steps
subdividing the parameter intervals into at least two sub-intervals determining a supra-parameter value for each sub-interval identifying on the basis of the supra-parameter values whether or not a course characteristic is present.

11. Method according to claim 10, wherein the at least two sub-intervals are of essentially equal size.

12. Method for detecting epileptic or psychogenic seizures, comprising the steps of:
   a. recording a large number of temporally sequential parameter values for a parameter type, wherein a parameter value is determined on the basis of a series of temporally sequential RR intervals,
   b. comparing the time course of the parameter values with the time course of parameter values for the same parameter type that had been determined according to method step a, and the determination thereof is based on RR intervals that indicate a seizure (parameter reference values),
   c. identifying a seizure when the time course of the parameter values exhibits a characteristic of the time course of the parameter reference values (course characteristic) indicating a seizure, further comprising the following method steps:
      forming temporally sequential intervals that comprise temporally sequential parameter values (parameter intervals), parameter intervals being temporally sequential such that a following parameter interval differs from the preceding parameter interval in that it includes, in place of the oldest parameter value of the preceding parameter interval, the parameter value temporally subsequent to the most recent parameter value of the preceding parameter interval,
      examining the parameter intervals one at a time to see whether the course characteristic occurs in the individual parameter interval, and still further comprising the following method steps
      subdividing the parameter intervals into sub-intervals of essentially equal size
      determining the mean of all the parameter values of each sub-interval
      identifying the course characteristic "linearly descending" when the mean value of each older sub-interval is greater than the mean value of each more recent sub-interval.

13. Method according to claim 12, wherein the parameter intervals are subdivided into four sub-intervals of essentially equal size.

14. Method for detecting epileptic or psychogenic seizures, comprising the steps of:
   a. recording a large number of temporally sequential parameter values for a parameter type, wherein a parameter value is determined on the basis of a series of temporally sequential RR intervals,
   b. comparing the time course of the parameter values with the time course of parameter values for the same parameter type that had been determined according to method step a, and the determination thereof is based on RR intervals that indicate a seizure (parameter reference values),
   c. identifying a seizure when the time course of the parameter values exhibits a characteristic of the time course of the parameter reference values (course characteristic) indicating a seizure, further comprising the following method steps:
      forming temporally sequential intervals that comprise temporally sequential parameter values (parameter intervals), parameter intervals being temporally sequential such that a following parameter interval differs from the preceding parameter interval in that it includes, in place of the oldest parameter value of the preceding parameter interval, the parameter value temporally subsequent to the most recent parameter value of the preceding parameter interval,
      examining the parameter intervals one at a time to see whether the course characteristic occurs in the individual parameter interval, and still further comprising the following method steps:
      subdividing the parameter intervals into four sub-intervals of essentially equal size,
      determining the mean of all the parameter values of each sub-interval
      subdividing the oldest sub-interval into four sub-intervals of equal size (sub-sub-intervals) and determining the mean of all the parameter values of each sub-sub-interval,
      for the oldest sub-interval, examining whether the mean value for each more recent sub-sub-interval is greater than the mean value for each older sub-sub-interval (linear ascent in the oldest sub-sub-interval),
      subdividing the most recent sub-interval into four sub-intervals of equal size (sub-sub-intervals) and determining the mean of all the parameter values of each sub-sub-interval,
      for the most recent sub-interval, examining whether the mean value for each older sub-sub-interval is greater than the mean value for each more recent sub-sub-interval (linear descent in the most recent sub-sub-interval),
      identifying the course characteristic "hill shape" when
         the oldest sub-sub-interval exhibits a linear ascent,
         the most recent sub-sub-interval exhibits a linear descent,
         the mean value of the oldest sub-interval is smaller than the mean value of the second-oldest sub-interval and
         the mean value of the second-most recent sub-interval is greater than the mean value of the most recent sub-interval.

* * * * *